United States Patent
Nogami et al.

(10) Patent No.: US 12,422,446 B2
(45) Date of Patent: Sep. 23, 2025

(54) PRETREATMENT METHOD OF AN AUTOMATIC ANALYZER

(71) Applicant: HITACHI HIGH-TECH CORPORATION, Tokyo (JP)

(72) Inventors: Makoto Nogami, Tokyo (JP); Shinya Matsuoka, Tokyo (JP); Daisuke Ebihara, Tokyo (JP); Yuichiro Hashimoto, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 1024 days.

(21) Appl. No.: 17/601,469

(22) PCT Filed: Mar. 9, 2020

(86) PCT No.: PCT/JP2020/009996
§ 371 (c)(1),
(2) Date: Oct. 5, 2021

(87) PCT Pub. No.: WO2020/225971
PCT Pub. Date: Nov. 12, 2020

(65) Prior Publication Data
US 2022/0276270 A1    Sep. 1, 2022

(30) Foreign Application Priority Data

May 8, 2019   (JP) .................... 2019-088019

(51) Int. Cl.
*G01N 35/00*   (2006.01)
*G01N 35/04*   (2006.01)

(52) U.S. Cl.
CPC ............ *G01N 35/0098* (2013.01); *G01N 2035/00356* (2013.01); *G01N 2035/00534* (2013.01); *G01N 2035/0446* (2013.01)

(58) Field of Classification Search
CPC . G01N 2035/0446; G01N 2035/00534; G01N 2035/00356; G01N 35/0098; G01N 27/745; G01N 33/54326
USPC ......... 435/962; 436/177, 178, 824, 825, 526
See application file for complete search history.

(56) References Cited

U.S. PATENT DOCUMENTS

| | | | |
|---|---|---|---|
| 9,236,236 B2 | 1/2016 | DeWitte et al. | |
| 11,402,386 B2 † | 8/2022 | Hudson | |
| 2002/0012929 A1 | 1/2002 | Malmqvist et al. | |
| 2003/0224534 A1 | 12/2003 | Kawate | |
| 2004/0077024 A1 | 4/2004 | Holmberg | |
| 2004/0132044 A1 * | 7/2004 | Ritterband | B03C 1/286 435/6.12 |
| 2011/0091903 A1 | 4/2011 | Bommarito et al. | |
| 2015/0309059 A1 | 10/2015 | Tajima | |
| 2017/0160273 A1 | 6/2017 | Nogami et al. | |
| 2018/0209945 A1 | 7/2018 | Sasano | |

FOREIGN PATENT DOCUMENTS

| | | | | |
|---|---|---|---|---|
| CN | 106574934 A | 4/2017 | | |
| CN | 107850581 A | 3/2018 | | |
| JP | 2003-527606 A | 9/2003 | | |
| JP | 2004-045395 A | 2/2004 | | |
| JP | 2004-527732 A | 9/2004 | | |
| JP | 2011-504236 A | 2/2011 | | |
| JP | 2016090570 A * | 5/2016 | | |
| JP | 2018-046848 A | 3/2018 | | |
| JP | 2019-049455 A | 3/2019 | | |
| WO | WO-9831840 A1 * | 7/1998 | ......... | C12N 15/1013 |
| WO | 2005/095969 A1 | 10/2005 | | |
| WO | 2006/088192 A1 | 8/2006 | | |
| WO | 2007/081387 A1 | 7/2007 | | |
| WO | 2014/077400 A1 | 5/2014 | | |
| WO | 2015/025378 A1 | 2/2015 | | |

OTHER PUBLICATIONS

Sasso et al., Automated microfluidic processing platform for multiplexed magnetic bead immunoassays. Oct. 2012, Microfluid Nanofluidics, 13(4), 603-612. (Year: 2012).*
Knol et al., ALDI-TOF Serum Profiling Using Semiautomated Serum Peptide Capture with Magnetic Reversed Phase (C18) Beads, 2011, Humana Press, 790, 3-16. (Year: 2011).*
He, Jincan, et al. "Magnetic separation techniques in sample preparation for biological analysis: a review." Journal of pharmaceutical and biomedical analysis 101 (2014): 84-101. (Year: 2014).*
Nemzek, J A et al. "Development and optimization of cytokine ELISAs using commercial antibody pairs." Journal of immunological methods vol. 255, 1-2 (2001): 149-57. doi: 10.1016/s0022-1759(01)00419-7 (Year: 2001).*
https://assets.thermofisher.com/TFS-Assets/LSG/manuals/MAN0011758_Pierce_NHSActiv_Mag_Bead_UG.pdf Product Manual (Year: 2013).*
Chinese Office Action received in corresponding Chinese Application No. 202080032039.5 dated Dec. 1, 2023.

(Continued)

*Primary Examiner* — Bao-Thuy L Nguyen
*Assistant Examiner* — Jim Atwell
(74) *Attorney, Agent, or Firm* — Mattingly & Malur, PC

(57) ABSTRACT

A pretreatment method of an automatic analyzer, in which pretreatments of a plurality of substances to be measured can be performed by a series of treatments using a plurality of magnetic beads that can bind to the plurality of substances to be measured, is achieved. In the pretreatment method of an automatic analyzer, a magnetic bead is added to a sample containing a substance to be measured, the substance to be measured is bound to the magnetic bead, the magnetic bead is extracted from the sample, and the substance to be measured is separated from the magnetic bead by an eluate. A plurality of magnetic beads that bind to a plurality of types of substances to be measured are added to a sample, and the plurality of types of substances to be measured are extracted from the magnetic bead by an eluate.

5 Claims, 14 Drawing Sheets

(56) References Cited

OTHER PUBLICATIONS

Extended European Search Report received in corresponding European Application No. 20802846.4 dated Dec. 20, 2022.
International Search Report of PCT/JP2020/009996 dated Jun. 2, 2020.
Chinese Office Action received in corresponding Chinese Application No. 202080032039.5 dated Apr. 11, 2024.
Translation of the International Preliminary Report on Patentability received in corresponding International Application No. PCT/JP2020/009996 dated Nov. 11, 2021.
Jeffrey R. Whiteaker, An Automated and Mutiplexed Method for High Throughput Peptide Immunoaffinity Enrichment and Multiple Reaction Monitoring Mass Spectrometry-based Quantification of Protein Biomarkers, Molecular & Cellular Proteomics 9.1, pp. 184-196, Oct. 20, 2009.†
Leigh Anderson, High Sensitivity SISCAPA-based Peptide Quantitation Using UHPLC and the 6490 QQQ with iFunnel Technology, Agilent Technologies Application Note, Aug. 7, 2014.†

\* cited by examiner
† cited by third party

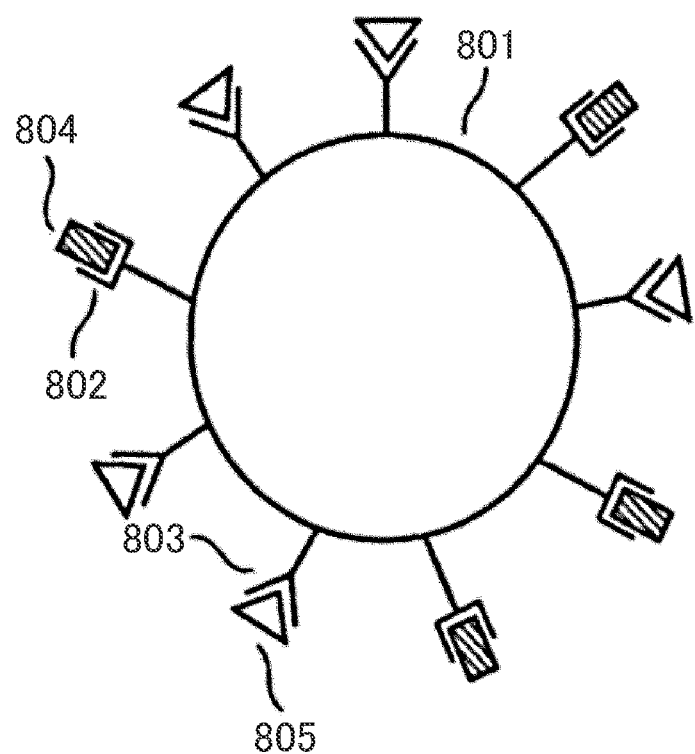

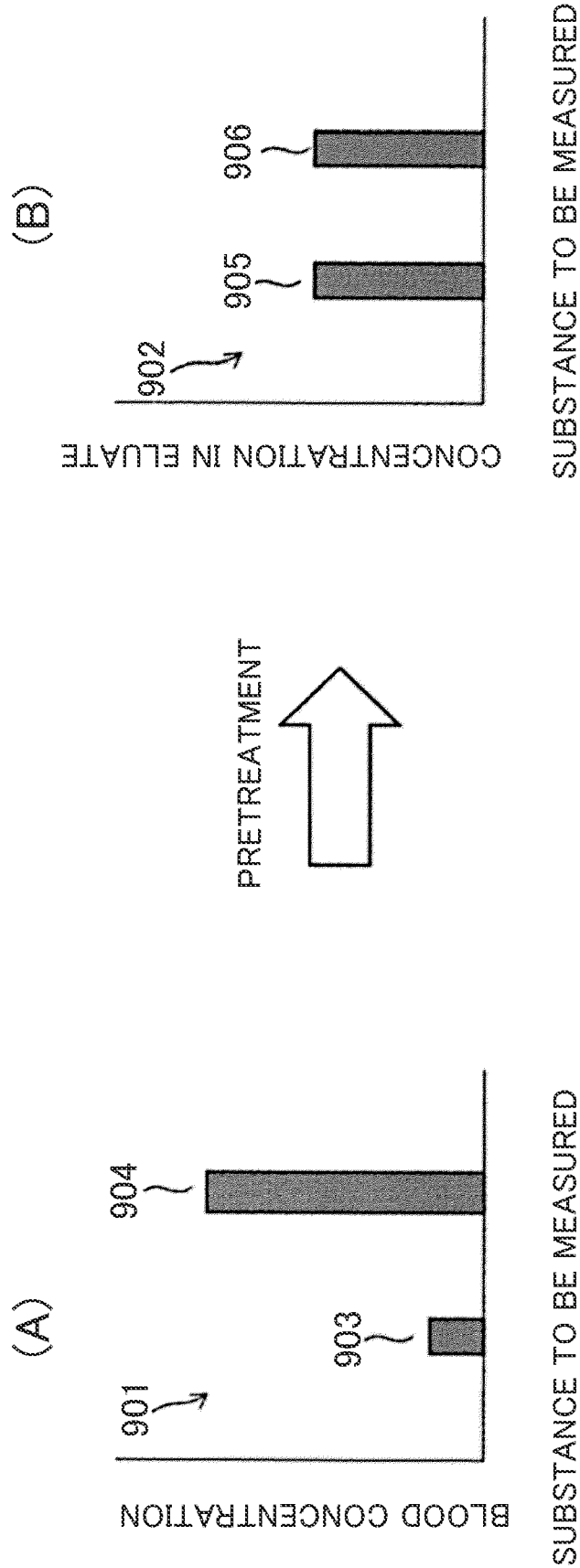

PRETREATMENT METHOD OF AN AUTOMATIC ANALYZER

TECHNICAL FIELD

The present invention relates to a pretreatment method of an automatic analyzer that analyzes a sample.

BACKGROUND ART

An automatic analyzer automates a part of a procedure of an inspection to contribute to a rapid and efficient clinical inspection task. Each of typical automatic analyzers includes a dispensing mechanism for dispensing a predetermined amount of a solution of a sample, a reagent, or the like into a reaction container, and a stirring mechanism that stirs the sample, the reagent, or the like in the reaction container. Among them, an immune system holds a substance to be measured with a carrier obtained by binding a functional group to a surface of a magnetic bead and uses electrochemiluminescence immunoassay (ECLIA), which is among immunoassay methods, to allow a high-accuracy, high-sensitivity, and wide-range inspection.

A high-performance liquid chromatograph mass spectrometer (HPLC/MS) is a device including a combination of a liquid chromatograph and a mass spectrometer.

By combining separation of substances to be measured based on chemical structures and physical properties thereof using the high-performance liquid chromatograph (HPLC) with separation of the substances to be measured based on masses thereof using a mass spectrometer (MS), it is possible to determine the quality/quantity of each of components in a sample. Due to this feature, even when, e.g., a large number of similar substances are mixed with each other as a result of metabolism inside a body such as that of a medical drug in a biological sample, it is possible to determine the quality/quantity of each of substances to be measured, and an application of the HPLC/MS to a clinical inspection field is expected.

In an inspection center, a university hospital, or the like, the HPLC/MS is used to inspect an immunosuppressing agent, an anticancer agent, or a newborn metabolic disorder and perform an inspection such as TDM (Therapeutic Drug Monitoring).

A pretreatment is performed using a test kit or a manual method to supply a sample to the HPLC/MS. Verification (variation) of each of inspection methods is performed under the responsibility of each of inspection institutes to ensure a result of an inspection.

Since a pretreatment step is complicated, depending on a degree of proficiency of a laboratory technician, a result of an inspection varies. In addition, in a pretreatment or HPLC/MS measurement, a human error may cause a defect in a result of an inspection.

Accordingly, it has been requested to expand an automatic analyzer capable of full-automatically performing a batch treatment step including a pretreatment and the HPLC/MS into the clinical inspection field.

As one of such automatic analyzers, an automatic analyzer capable of full-automatically performing the batch step including the pretreatment and the HPLC/MS is disclosed in Patent Literature 1.

A pretreatment step of a typical immune system uses a method which sends, into a solution sending flow path, a solution in a state where a substance to be measured is bonded to a functional group of each of magnetic beads, magnetically collects the magnetic beads in the flow path, and performs measurement using electrochemiluminescence. The ECLIA, which is among methods used in the immune system, is a method in which, after a bead having an antibody bonded thereto is used to react the antibody with an antigen, an antibody labeled with a ruthenium pyridine complex is secondarily reacted with the antigen, and an intensity of emission from the ruthenium pyridine complex is measured using an electrochemical reaction and which uses one type of magnetic bead to which an antibody for one substance to be measured is bonded.

Meanwhile, methods using a plurality of beads include a fluorescent imunnostaining method, DNA microarray analysis, in-situ immuno-hybridization, and the like. The fluorescent immunostaining method is a method in which magnetic beads each having a primary antibody conjugated with a fluorochrome and bonded to a surface thereof are bonded to a substance to be measured, and a labeled secondary antibody is bound to the primary antibody to enhance a fluorescent signal.

The DNA microarray analysis is a method which binds minute beads to a cDNA or rDNA as a plurality of fluorescently labeled nucleic acid templates, reacts the cDNA or rDNA with a target DNA, and observes development of colors.

The in-situ immuno-hybridization is a method which binds a nucleic acid template to a DNA or RNA without extracting the DNA or RNA, and observes development of colors.

As a color development method, organic dyeing such as Cy3 or Cy5 or a solution containing a dye such as used for an inorganic label such as a quantum dot is used. Even in a method using one type of magnetic bead, when a polyclonal antibody, not a highly specific monoclonal antibody, is conjugated with a surface of the magnetic bead, it is possible to allow the one type of magnetic bead to bind to a plurality of substances to be measured.

Patent Literature 2 discloses the invention in which the method described above is inclusively implemented in a microreactor.

As a typical pretreatment for the HPLC/MS, it has been practiced to bind a substance to be measured to a filler by using solid phase extraction, and then perform the extraction in multiple stages by using a plurality of types of eluates. For example, in the case of the solid phase extraction in which a C18 filler is sealed, there is a method which separates a substance to be measured from foreign substances by using a plurality of eluates having different organic solvent concentrations.

CITATION LIST

Patent Literatures

Patent Literature 1: U.S. Pat. No. 9,236,236
Patent Literature 2: Japanese Unexamined Patent Application Publication No. 2018-46848

SUMMARY OF INVENTION

Technical Problem

In a pretreatment method of an automatic analyzer using magnetic beads, it is desired to improve a throughput, reduce a quantity of samples, and improve inspection accuracy.

As a pretreatment method of the automatic analyzer disclosed in Patent Literature 1, a pretreatment method using liquid/liquid extraction and the solid phase extraction is used. However, there is no description of a pretreatment method using magnetic beads, and it is difficult to achieve improved inspection accuracy or the like for a pretreatment using magnetic beads.

In a pretreatment method using magnetic beads in a pretreatment step of an automatic analyzer using the HPLC/MS as a detector, such as used in a magnetic bead immune system, a solution in which only a substance to be measured has been eluted by binding the substance to be measured to a functional group of each of the magnetic beads, performing cleaning, and then adding an eluting solution thereto in a state where the magnetic beads are magnetically collected is supplied as a sample to the HPLC/MS.

In addition, to improve quantity determination accuracy in the MS, it is also required to add a stable isotope substance of the substance to be measured.

Since a pretreatment method using magnetic beads includes the number of steps larger than that of steps included in a typical immune system, a treatment time period is longer than in the typical immune system, and it is required to improve a throughput.

Various methods using beads conjugated with antibodies and a fluorescent label, which are disclosed in Patent Literature 2, measure development of colors from a fluorescently labeled body. Therefore, there is no need to eventually separate the beads from the substance to be measured.

Meanwhile, the present automatic analyzer targeted by the present invention and capable of full-automatically performing the batch step including the pretreatment and the HPLC/MS requires an elution step of separating the beads from the substance to be measured in the pretreatment step to perform separation/detection with the HPLC/MS.

Moreover, in Patent Document 2, there is no disclosure of a method and timing for the elution step required to improve a throughput without degrading inspection accuracy when the plurality of magnetic beads are used.

Note that, in the case of the solid phase extraction, it is unnecessary to use magnetic beads for the filler, and there is no step of performing stirring and magnetically collecting magnetic beads, unlike in the pretreatment step targeted by the present invention.

An object of the present invention is to perform a pretreatment method of an automatic analyzer that binds a substance to be measured to a magnetic bead to perform treatment and full-automatically performs a batch step including pretreatment and a liquid chromatograph mass spectrometer, in which a plurality of the magnetic beads to which a plurality of the substances to be measured can be bound are used to allow the plurality of substances to be measured to be pretreated by a sequential treatment.

Solution to Problem

To attain the object described above, the present invention is configured as follows.

In a pretreatment method of an automatic analyzer comprising the steps of: adding a magnetic bead to a sample containing a substance to be measured; binding the substance to be measured to the magnetic bead; extracting the magnetic bead from the sample; and separating, by an eluate, the substance to be measured from the magnetic bead, a plurality of magnetic beads that bind to a plurality of types of substances to be measured are added to the sample, and the plurality of types of substances to be measured are separated from the magnetic beads by the eluate.

Advantageous Effects of Invention

According to the present invention, it is possible to perform a pretreatment method of an automatic analyzer that binds a substance to be measured to a magnetic bead to perform treatment and full-automatically performs a batch step including pretreatment and a liquid chromatograph mass spectrometer, in which a plurality of the magnetic beads to which a plurality of the substances to be measured can be bound are used to allow the plurality of substances to be measured to be pretreated by a sequential treatment.

BRIEF DESCRIPTION OF DRAWINGS

FIG. 8A is a view illustrating a concept of a magnetic bead having a plurality of functional groups in Third Embodiment.

FIG. 9 is a conceptual view illustrating quantity ratios between substances to be measured before and after a pretreatment in which a magnetic bead having a plurality of functional groups in Third Embodiment is used.

DESCRIPTION OF EMBODIMENTS

Figure 1:
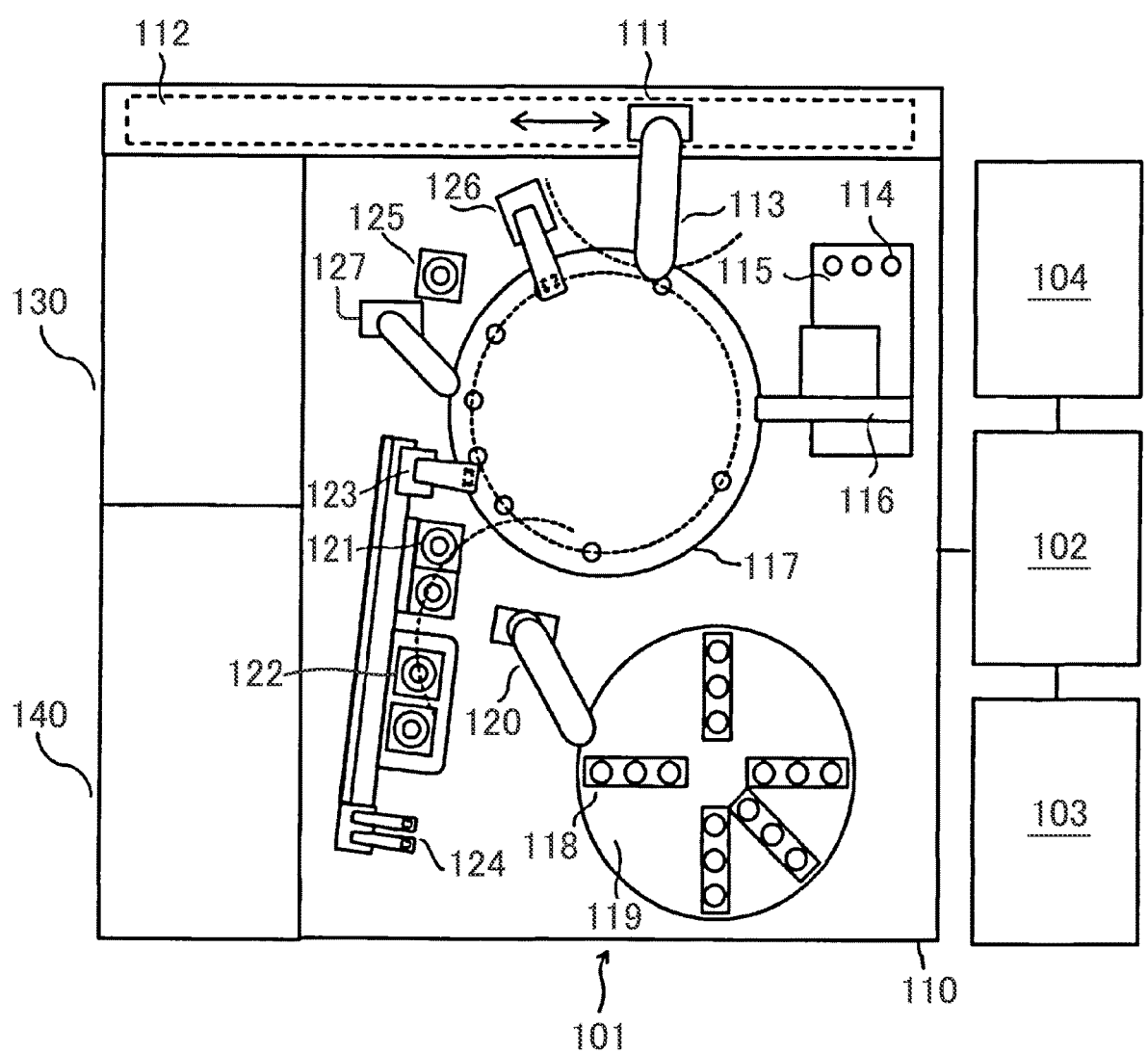
FIG. 1 is a schematic view of an automatic analyzer that performs a pretreatment method according to the present invention.

Referring to the drawings, a description will be given of embodiments of the present invention. Note that the embodiments described below mainly target an automatic analyzer, but the present invention is applicable to analyzers in general. The present invention is also applicable to, e.g., a gene analyzer or a bacteria tester.

EMBODIMENTS

First Embodiment

FIG. 1 is a schematic view of an automatic analyzer that performs a pretreatment method according to First Embodiment of the present invention.

In FIG. 1, an automatic analyzer 1 includes an analysis section 101 for performing an analyzing operation, a control section 102 for controlling an operation of the entire analyzer, an input section 103 for a user to input information to the analyzer, and a display section 104 for displaying information to the user. Note that the input section 103 and the display section 104 may also be the same section and, as an example thereof, a touch-panel monitor can be used.

The analysis section 101 of the automatic analyzer 1 includes a pretreatment section 110, a HPLC section 130, and a detector 140.

The analysis section 101 includes a sample container transport mechanism 112 for transporting sample containers 111 containing samples to a sample splitting position, a sample dispensing mechanism 113 for ejecting each of the samples, a reaction container mounting rack 115 on which reaction containers 114 are mounted, a reaction container transport mechanism 116 for transporting the reaction containers 114, and a reaction container disk 117 capable of holding the plurality of reaction containers 114.

The analysis section 101 also includes a reagent disk 119 for holding measuring reagent containers 118 containing measuring reagents, a reagent dispensing mechanism 120 that ejects the measuring reagents into the reaction containers 114, a stirring mechanism 121 that stirs a liquid contained in each of the reaction containers 114 in non-contact relation, a first magnetism collecting mechanism 122 that magnetically collects magnetic beads, a first transport mechanism 123 that transports the reaction containers 114 between the reaction container disk 117, the stirring mechanism 121, and the first magnetism collecting mechanism 122, and an effluent dispensing mechanism 124 that dispenses an effluent from the first magnetism collecting mechanism 122.

The analysis section 101 further includes a second magnetism collecting mechanism 125 that magnetically collects the magnetic beads, a second transport mechanism 126 that transports the reaction containers 114 between the reaction container disk 117 and the second magnetism collecting mechanism 125, and an eluate dispensing mechanism 127 that introduces an eluate into the HPLC section 130.

Figure 2:
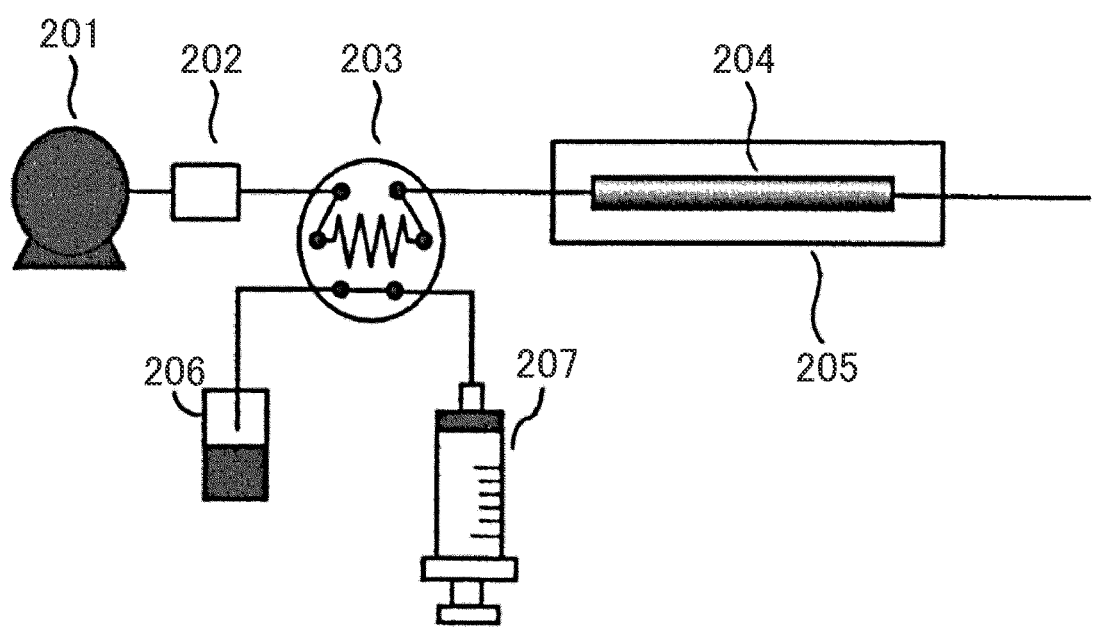
FIG. 2 is a schematic configuration view of an HPLC section.

FIG. 2 is a schematic configuration view of the HPLC section 130.

In FIG. 2, the HPLC section 130 includes a pump 201 that sends a solution of the sample (pretreated eluate), a pressure sensor 202 that measures a system pressure, and a 6-direction 2-position injection valve 203 including a sample loop that measures the sample (pretreated eluate).

Meanwhile, the HPLC section 130 includes a column 204, a column oven 205 that adjusts a temperature of the column 204, a sample vial 206 that holds the sample (pretreated eluate), and a syringe 207 that introduces the sample from the sample vial 206 into the sample loop.

In the case of changing a composition of the sample to allow a substance to be measured to bind to the column 204, the HPLC section 130 also includes a mechanism that adds a diluent to the sample vial 206, though not illustrated.

On the detector 140 illustrated in FIG. 1, a mass spectrometer is mounted. The mass spectrometer includes an ionization section that applies a high temperature and a high voltage to a solution containing the substance to be measured that has been separated by the HPLC section 130 and a triple-quadrupole mass spectrometer that separates the substance to be measured from foreign substances depending on a mass number, though illustration thereof is omitted. The triple-quadrupole mass spectrometer is used to measure a component to be measured in a SRM (Selected Reaction Monitoring) mode.

Referring to FIG. 1, a description will be given below of an outline of an analysis step by the automatic analyzer.

Prior to analysis, the automatic analyzer 1 uses the reaction container transport mechanism 116 to transport the reaction containers 114 from the reaction container mounting rack 115 and place the reaction containers 114 on the reaction container disk 117.

The sample dispensing mechanism 113 suctions the sample from each of the sample container 111 transported by the sample container transport mechanism 112 and ejects the sample into each of the reaction containers 114 on the reaction container disk 117. As the sample dispensing mechanism 113, a dispensing mechanism involving no replacement of a chip is used in First Embodiment, but it may also be possible to use a disposable dispensing mechanism which uses a dispensing chip attachment/detachment section (not shown) to attach a dispensing chip to a tip portion prior to the suction of the sample. In the case of the disposable dispensing mechanism, when dispensing of the sample from one of the sample containers 111 is ended, the sample dispensing mechanism 113 discards the dispensing chip into the dispensing chip attachment/detachment section. Each of the reaction containers 114 on the reaction container disk 117, into which the sample has been dispensed, is transported by the first transport mechanism 123 to the stirring mechanism 121. After stirring of the sample in the reaction container 114, the reaction container 114 is returned by the first transport mechanism 123 to the reaction container disk 117.

The reagent dispensing mechanism 120 suctions the measuring reagent from each of the measuring reagent containers 118 on the reagent disk 119, and ejects the measuring reagent into the reaction container 114. An operating portion of the reagent dispensing mechanism 120 can access each of the reaction container disk 117 and the stirring mechanism 121 and, after the stirring mechanism 121 begins to stir a liquid contained in the reaction container 114, the reagent dispensing mechanism 120 begins to eject the reagent in a state where the reaction container 114 is held by the stirring mechanism 121.

For example, the stirring mechanism 121 stirs the liquid in the reaction container 114 before the reagent dispensing mechanism 120 finishes ejecting a predetermined amount of the reagent into the reaction container 114. This reduces a possibility of generation of an insoluble material compared to that in a case where the stirring of the solution is started after the reagent dispensing mechanism 120 finishes ejecting a large amount of the reagent.

Note that the predetermined amount of the reagent means the reagent in an amount corresponding to that of a portion of the reagent suctioned by the reagent dispensing mechanism 120 from the measuring agent container 118. The reagent dispensing mechanism 120 may also operate simultaneously with the stirring mechanism 121 or operate while the stirring mechanism 121 is stopped.

A solution mixture of the sample and the reagent contained in the reaction container 114 is stirred by the stirring mechanism 121 to form a flow. The ejection and stirring of the reagent may also be such that, after the reagent dispensing mechanism 120 ejects the reagent into the reaction container 114 on the reaction container disk 117, the reaction container 114 is transported by the first transport mechanism 123 to the stirring mechanism 121, and the solution mixture is stirred.

The reaction container 114 after the ejection of the reagent by the reagent dispensing mechanism 120 and the stirring by the stirring mechanism 121 ended is placed again on the reaction container disk 117 by the first transport mechanism 123. The reaction container disk 117 functions as, e.g., an incubator to incubate the held reaction container 114 during a given period of time.

The magnetic beads are stored (contained) in the measuring reagent container 118 and ejected using the reagent dispensing mechanism 120 into the reaction container 114. In the reaction container 114, the substance to be measured in the sample binds to the magnetic beads. Then, the reaction container 114 is transported by the first transport mechanism 123 to the first magnetism collecting mechanism 122, and the magnetic beads are adsorbed to a side surface of the reaction chamber 114.

The effluent dispensing mechanism 124 has two shippers mounted thereon and has a mechanism capable of suctioning/ejecting an effluent and ejecting a cleaning liquid. The effluent dispensing mechanism 124 moves to the first magnetism collecting mechanism 122 to suction the solution, and the magnetic beads are extracted from the sample. Then, the effluent dispensing mechanism 124 moves to an effluent ejection position to eject the effluent. The effluent dispensing mechanism 124 moves to the first magnetism collecting mechanism 122 to eject the cleaning liquid into each of the reaction containers 114. The reaction container 114 into which the cleaning liquid was ejected is transported by the first transport mechanism 123 to the stirring mechanism 121, and stirring is performed.

Then, the reaction container 114 is transported by the first transport mechanism 123 to the first magnetism collecting mechanism 122, and the suction/ejection of the cleaning liquid is performed by the effluent dispensing mechanism 124. When the cleaning is to be performed a plurality of times, the suction/ejection of the effluent and the ejection of the cleaning liquid is performed a plurality of times. The stirring mechanism 121 and the first magnetism collecting mechanism 122 are provided at each of two places in each of the mechanisms to allow cleaning treatment to be simultaneously performed in parallel on the plurality of reaction containers 114.

After being cleaned, each of the reaction containers 114 is returned by the first transport mechanism 123 to the reaction container disk 117. In the reaction container 114, the cleaned magnetic beads are held. An eluate stored in the measuring reagent container 118 is ejected by the reagent dispensing mechanism 120 into the reaction container 114, and the substance to be measured is separated from the magnetic beads. Then, the reaction container 114 is transferred by the first transport mechanism 123 to the stirring mechanism 121 and returned, after stirring was performed, into the reaction container disk 117 to be incubated. The eluate is compliant with a type of the magnetic beads.

By the second transport mechanism 126, the incubated reaction container 114 is transported to the second magnetism collecting mechanism 125, and the magnetic beads are adsorbed to the side surface of the reaction container 114. The detector dispensing mechanism 127 suctions the eluate in the reaction container 114 and transports the eluate to the HPLC section 130.

Using FIGS. 3A, 3B, 4A, 4B, and 4C each of which is an explanatory view of an operation of the injection valve 203, a description will be given of a method of introducing the sample into the HPLC section 130.

Figure 3A:
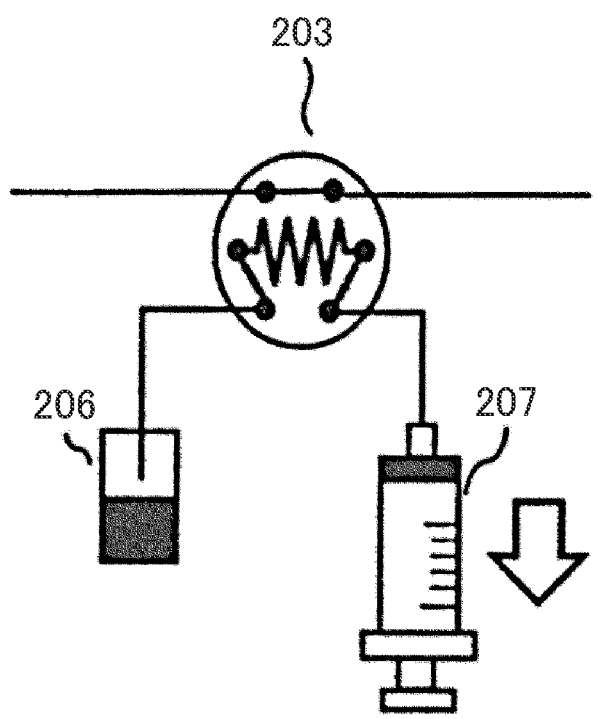
FIG. 3A is an explanatory view of an operation of an injection valve of the HPLC section.

As illustrated in FIG. 3A, in a state where the injection valve 203 is at a first position (position providing connection between the sample vial 206 and the sample loop syringe 207), the injection valve 203 drives the singe 207 in a direction of the suction to draw the sample in the sample vial 206 into the sample loop.

Figure 3B:
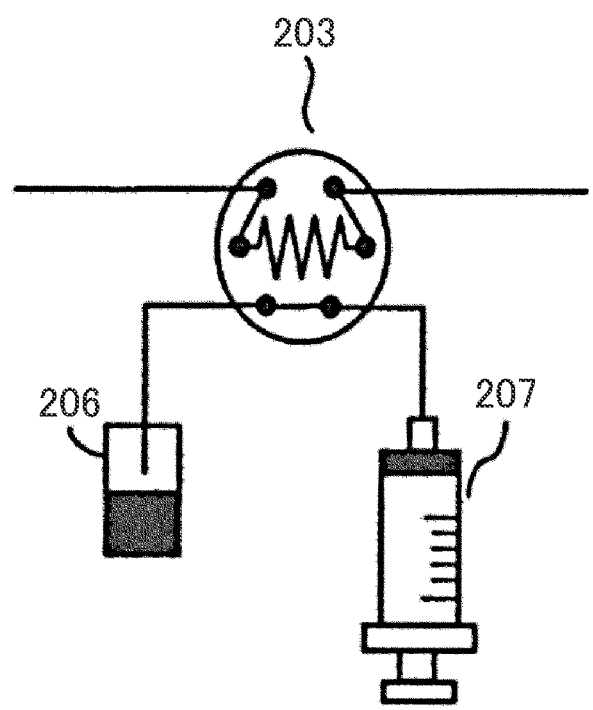
FIG. 3B is an explanatory view of an operation of the injection valve of the HPLC section.

Then, as illustrated in FIG. 3B, the injection valve 203 is shifted to a second position (position at which the sample loop is separated from the sample vial 206 and from the syringe 207) to provide a method in which the sample is drawn into the HPLC section 130.

Figure 4A:
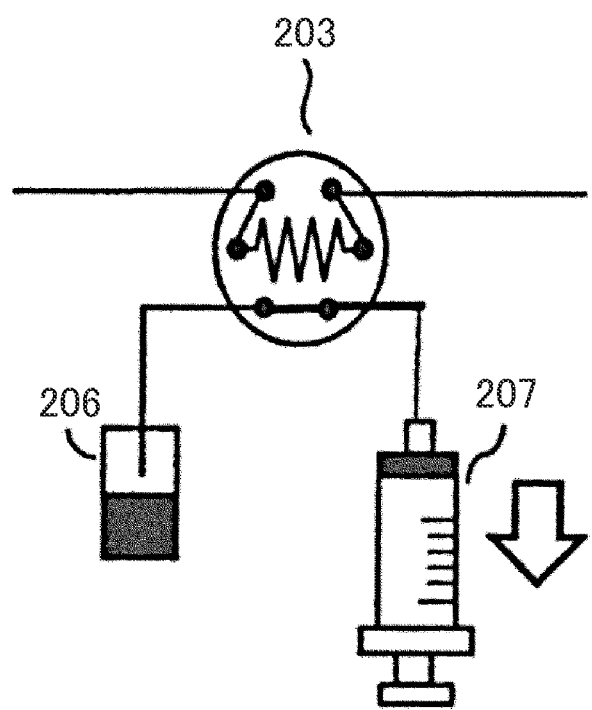
FIG. 4A is an explanatory view of an operation of the injection valve of the HPLC section.
Figure 4B:
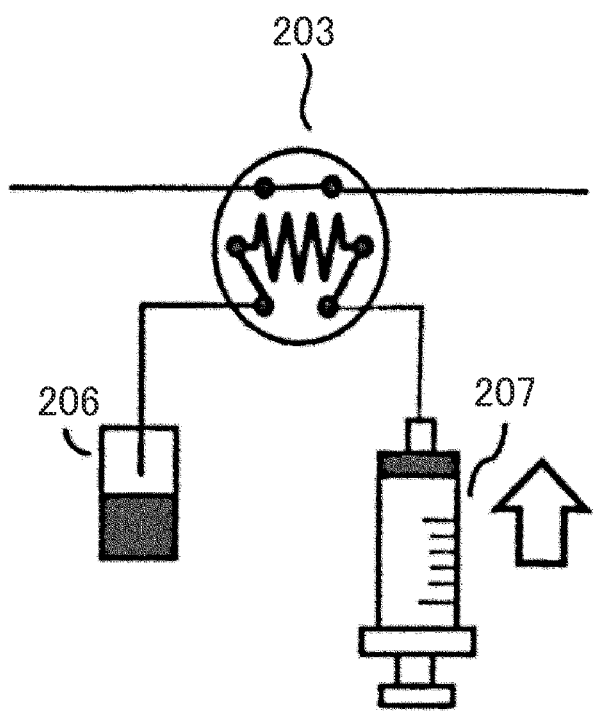
FIG. 4B is an explanatory view of an operation of the injection valve of the HPLC section.
Figure 4C:
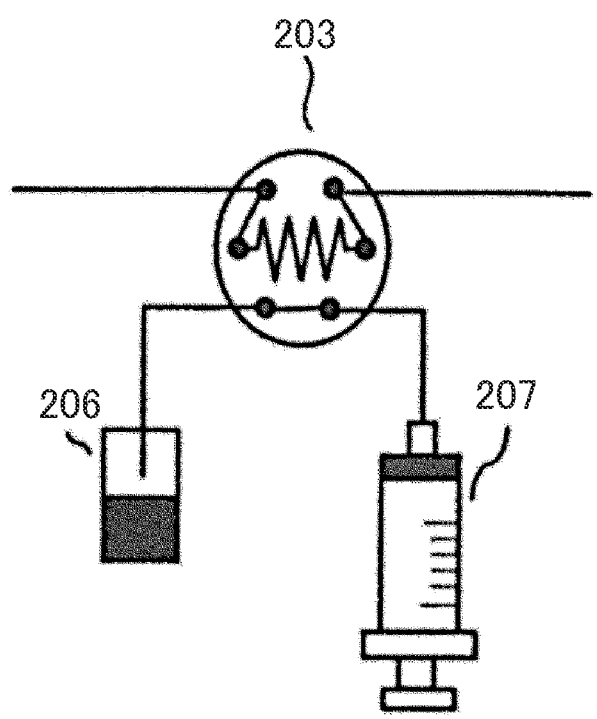
FIG. 4C is an explanatory view of an operation of the injection valve of the HPLC section.

In addition, a method can be provided in which the sample is introduced into the HPLC section 130 according to a method illustrated in FIGS. 4A, 4B, and 4C.

In other words, as illustrated in FIG. 4A, it is possible to provide a method in which, at the second position of the injection valve 203 (position providing connection between the sample vial 206 and the syringe 207), the sample is drawn to a syringe side. Then, as illustrated in FIG. 4B, the injection valve 203 is switched to the first position (position providing connection between the sample vial 206 and the sample loop syringe 207) to squeeze the sample into the sample loop with the syringe pump 207. Then, as illustrated in FIG. 4C, it is possible to provide a method in which the injection valve 203 is switched to the second position to introduce the sample into the HPLC section 130.

A solution containing the substance to be measured that has been separated by the HPLC section 130 is introduced into the detector 140. On the detector 140, a mass spectrometer is mounted, the ionization section ionizes the solution and introduces the ionized solution to the triple-quadrupole mass spectrometer, and measurement is performed. In data analysis, a ratio among area values is acquired and, using a calibration curve produced from a sample having a known concentration, a concentration of the sample is calculated.

As the mass spectrometer, a mass spectrometer of another type, such as a quadrupole mass spectrometer or an ion trap mass spectrometer, can also be used. The detector 140 need not necessarily be a mass spectrometer, and may also be a DAD (Diode Array Detector), a UV detector, gas chromatography, or an NMR.

In First Embodiment, a description will be given of an assay protocol in the case of two types of magnetic beads (a magnetic bead (first magnetic bead) having a surface modified with an antibody as a functional group and a magnetic bead (second magnetic bead) having a surface modified with a negative-phase-mode functional group (an example of which is an ODS (octadecylsilyl group))). The first magnetic beads first reacts with the substance to be measured before the second magnetic bead.

The ODS provides a magnetic bead obtained by reacting a silane coupling agent such as a dimethyloctadecylsilane with porous silica gel and having a surface modified with an octadecyl group. The substance to be measured in the sample is bonded to the magnetic bead by hydrophobic interaction to be eluted using an organic solvent or the like.

First, a description will be given of the case of one type of magnetic beads (Functional Groups: ODS Beads).

Figure 5:
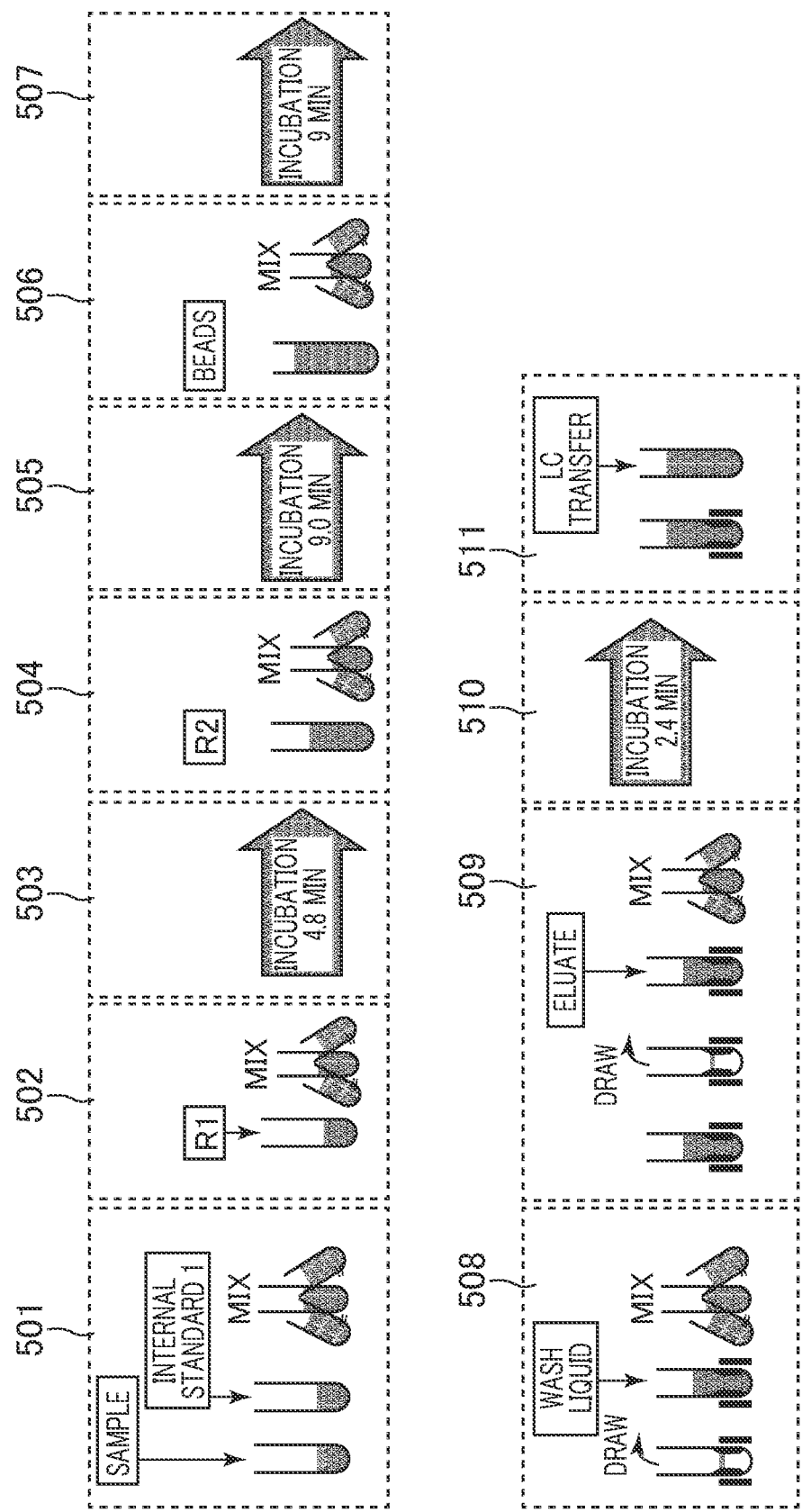
FIG. 5 is an explanatory view of an assay protocol in which one type of magnetic beads are used.

FIG. 5 is an explanatory view of an assay protocol when one type of magnetic beads (Functional Groups: ODS Beads) are used. A description will be given of a case where testosterone as a type of steroid hormone is used as the substance to be measured.

In FIG. 5, the assay protocol requires a total of 51 cycles, and requires 30.6 minutes. Accordingly, a time period of each one of the cycles is set to 36 seconds.

In First Embodiment, each one of the cycles is set to 36 seconds, but each one of the cycles may also be longer than 36 seconds. The following will describe each of the cycles. Treatment steps 501 to 511 are pretreatment steps when the one type of magnetic beads are used. However, it is also possible to define the treatment steps 501 to 509 as pretreatment steps when the one type of magnetic beads are used.

In Cycle 1 (the treatment step 501), addition and stirring of a sample and an internal standard substance is performed.

In Cycle 2 (the treatment step 502), addition and stirring of a first reagent is performed.

In Cycles 3-10 (the treatment step 503), incubation is performed (4.8 minutes).

In Cycle 11 (the treatment step 504), addition and stirring of a second reagent is performed.

In Cycles 12-26 (the treatment step 505), incubation is performed (9.0 minutes).

In Cycle 27 (the treatment step 506), addition and stirring of the magnetic beads is performed.

In Cycles 28-42 (the treatment step 507), incubation is performed (9.0 minutes).

In Cycles 43-45 (the treatment step 508), addition and stirring of a cleaning liquid is performed.

In Cycle 46 (the treatment step 509), addition and stirring of an eluate is performed.

In Cycles 47-50 (the treatment step 510), incubation is performed (2.4 minutes).

In Cycle 51 (the treatment step 511), transfer of the eluate to the HPLC section 130 is performed.

Note that the sample added in Cycle 1 is blood serum, and 100 μL of the blood serum was added. The sample need not necessarily be the blood serum, and may also be blood plasma, whole blood, urine, a cell tissue, a blood cell, or the like. As the internal standard substance, 100 μL of 100 pg/mL testosterone-2,3,4-13C3 was added. However, the internal standard substance may also be testosterone-D3.

As the first reagent added in Cycle 2, 10 μL of a 0.1% aqueous formic acid solution serving as a pH adjustment reagent was added. The incubation was performed at 37° C. The second reagent added in Cycle 11 is not used in First Embodiment, but typically serves as a second pH adjustment reagent, a protein denaturation reagent, or the like.

The magnetic beads added in Cycle 27 were stirred before being added (a stirring mechanism for the magnetic beads is not shown), and then 100 μL of the magnetic beads were added. As the cleaning liquid added in Cycles 43-45, 100 μL of pure water was added. As the eluate added in Cycle 46, 50 μL of a 80% methanol solution was added.

Figure 6:
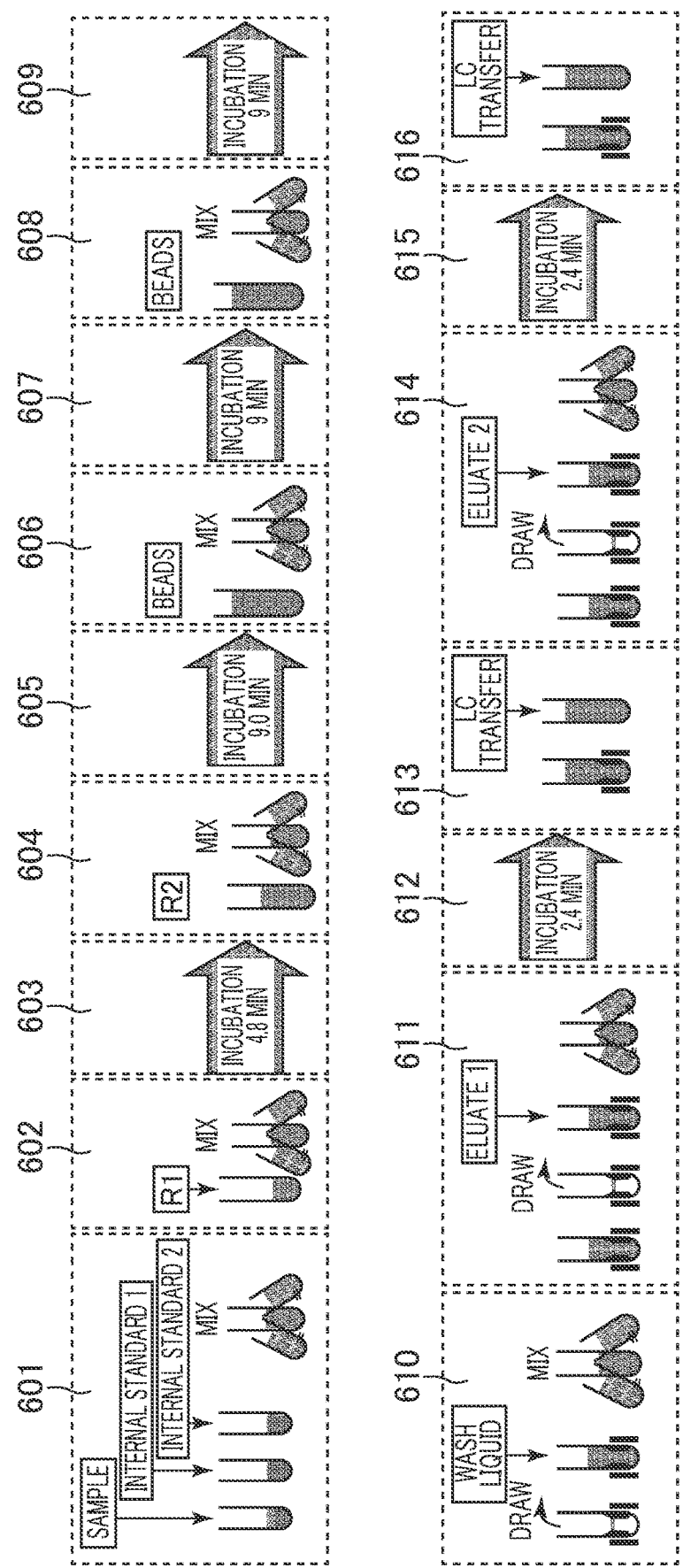
FIG. 6 is an explanatory view of an assay protocol of First Embodiment, in which two types of magnetic beads are used.

FIG. 6 is an explanatory view of an assay protocol in the case of First Embodiment in which two types of magnetic beads (Functional Groups: ODS Beads and Antibody Beads) are used. A description will be given of a case where two types of subjects to be measured, which are testosterone as a type of steroid hormone and gentamicin as a type of aminoglycoside antimicrobial, are to be measured.

The assay protocol requires a total of 74 cycles, and requires 44.4 minutes. Accordingly, a time period of each one of the cycles is set to 36 seconds. In First Embodiment, each one of the cycles is set to 36 seconds, but each one of the cycles may also be longer or shorter than 36 seconds. The following will describe each of the cycles. Treatment steps 601-616 are pretreatment steps when the two types of magnetic beads are used. However, it is also possible to define the treatment steps 601-611 and 614 as pretreatment steps when the two types of magnetic beads are used.

In Cycles 1-2 (the treatment Step 601), addition and stirring of a sample, a first internal standard substance, and a second internal standard substance is performed.

In Cycle 3 (the treatment Step 602), addition and stirring of the first reagent (R1) is performed.

In Cycles 4-11 (the treatment Step 603), incubation is performed (4.8 minutes).

In Cycle 12 (the treatment Step 604), addition and stirring of the second reagent (R2) is performed.

In Cycles 13-27 (the treatment Step 605), incubation is performed (9.0 minutes).

In Cycle 28 (the treatment Step 606), addition and stirring of first magnetic beads is performed.

In Cycles 29-43 (the treatment Step 607), incubation is performed (9.0 minutes).

In Cycle 44 (the treatment Step 608), addition and stirring of second magnetic beads is performed.

In Cycles 45-59 (the treatment Step 609), incubation is performed (9.0 minutes).

In Cycles 60-62 (the treatment Step 610), addition and stirring of a cleaning liquid is performed.

In Cycle 63 (the treatment Step 611), addition and stirring of a first eluate is performed.

In Cycles 64-67 (the treatment Step 612), incubation is performed (2.4 minutes).

In Cycle 68 (the treatment Step 613), transfer of the eluate to the HPLC section 130 is performed.

In Cycle 69 (the treatment Step 614), addition and stirring of a second eluate is performed.

In Cycles 70-73 (the treatment Step 615), incubation is performed (2.4 minutes).

In Cycle 74 (the treatment Step 616), transfer of the eluate to the HPLC section 130 is performed.

The sample added in Cycles 1-2 (the treatment Step 601) was 100 μL of blood serum. As the internal standard substance for gentamicin, 100 μL of 1 μg/mL tobramycin was added and, as the internal standard substance for testosterone, 100 μL of 100 μg/mL testosterone-2,3,4-13C3 was added.

As the first reagent added in Cycle 3 (the treatment Step 602), 10 μL of the 0.1% aqueous formic acid solution serving as the pH adjustment reagent was used. The incubation was performed at 37° C. The second reagent added in Cycle 12 (the treatment Step 604) is not used in First Embodiment, but typically serves as a second pH adjustment reagent, a protein denaturation agent, or the like.

The magnetic beads 1 added in Cycle 28 (the treatment Step 606) are magnetic beads each having, in a functional group, an antibody that specifically binds to a structure of an aminoglycoside antimicrobial, and 1 μL of the magnetic beads were added. The second magnetic beads added in Cycle 44 (the treatment Step 608) are magnetic beads each having the ODS in a functional group, and 100 μL of the magnetic beads were added.

The cleaning liquid added in Cycles 60-62 (the treatment Step 610) was pure water, and 100 μL of the pure water was added. The first eluate added in Cycle 63 (the treatment Step 611) was a 0.1% glycine sodium solution (pH 10.0) as a high pH solution, and 50 μL of the 0.1% glycine sodium solution was added. An eluate usable as the eluate for the first magnetic beads each having the antibody in the functional group is limited depending on the type of the second magnetic beads. In First Embodiment, the magnetic beads each having the ODS in the functional group are used as the second magnetic beads, and accordingly a solvent which is a high pH organic solvent cannot be used. Besides 0.1% glycine sodium solution (pH 10.0), a 100 mM glycine hydrochloric acid solution (pH 3.0) as a low pH solution, 8 mol/L urea serving as a denaturation agent, or 6 mol/L glycine hydrochloride may also be used.

The second eluate added in Cycle 69 (the treatment Step 614) was a 80% methanol solution, and 60 μL of the 80% methanol solution was added.

In First Embodiment, the two types of magnetic beads each having a surface modified with the functional groups including the ODS and the antibody were used, but another mode may also be used. For example, HILIC, a positive phase, ion exchange, GPC (molecular weight cut-off), or SFC (supercritical fluid chromatography) may also be used. This is appropriately selected depending on physical properties two types of substances to be measured, and a magnetic bead having a high adsorptive specificity is preferably selected for each of the substances to be measured. For example, for a highly hydrophilic substance to be measured, a magnetic bead having a surface modified with a positive-phase-mode functional group is used. For a highly hydrophobic substance to be measured, a magnetic bead having a surface modified with a negative-phase-mode functional group is used.

The first magnetic beads added in Cycle 28 (the treatment Step 606) and the second magnetic beads added in Cycle 44 (the treatment Step 608) are added such that the magnetic beads modified with more highly specific functional groups are added as the first magnetic beads in cycles having smaller numbers. More highly specific magnetic beads are magnetic beads each having a surface modified with, e.g., an antibody. By adding the more highly specific magnetic beads earlier and treating the substances to be measured in the sample, accuracy of reproducibility is improved.

The respective quantities of the magnetic beads added in Cycle 28 (the treatment Step 606) and Cycle 44 (the treatment Step 608) are such that 1 μL of the first magnetic beads were added and 100 μL of the second magnetic beads were added in First Embodiment, but the quantities of the first and second beads can appropriately be changed depending on a quantity ratio between the substance to be measured which are contained in the sample. For example, when the first substance to be measured is on an order of several picograms per milliliters and the second substance to be measured is on an order of several micrograms per milliliters, by adjusting the quantities of the magnetic beads to be added and the concentrations of the magnetic beads to be stored in the measurement reagent containers 118, it is possible to equalize the concentrations of the individual substances to be measured to be contained in the solution after the pretreatment.

When a concentration ratio between the substances to be measured to be contained in the solution after the pretreatment is high (e.g., about 1000:1), peaks after the separation in the HPLC section 130 overlap each other and, when the substances to be measured are simultaneously introduced at the same time into the detector 140, the substance to be measured at a higher concentration is preferentially ionized by the ionization section.

Consequently, the efficiency of ionization of the substance to be measured at a lower concentration deteriorates to degrade reproducibility. Accordingly, by equalizing the concentration ratio between the plurality of substances to be measured to be contained in the eluate after the pretreatment, measurement accuracy is improved.

Thus, according to First Embodiment of the present invention, by using the plurality of types of magnetic beads that can bind to the plurality of types of substances to be measured in one assay protocol, it is possible to pretreat the plurality of substances to be measured by a sequential pretreatment. In this case, the number of the cycles in each one assay protocol increases but, since it is possible to treat the plurality of types of substances to be measured, the pretreatment is performed cycle by cycle in parallel to increase the number of tests per time period and allow a throughput improvement.

In First Embodiment, each one of the cycles is set to 36 seconds (0.6 minutes). Accordingly, if one type of magnetic beads are used, since one assay protocol includes 51 cycles, 30.6 minutes is required.

By contrast, when two types of magnetic beads are used, since one assay protocol includes 74 cycles, 44.4 minutes is required. When the two types of magnetic beads are used, two types of substances to be measured can be treated in each one assay protocol and, accordingly, after the initial sample went through one assay protocol, a throughput is improved to about double a throughput when the one type of beads are used.

In addition, since the quantity of the samples used in one assay protocol is equal, the quantity of the samples for one substance to be measured that can be treated is approximately halved, which can save the quantity of the samples.

In other words, according to First Embodiment, it is possible to perform the pretreatment method of the automatic analyzer that can pretreat the plurality of substances to be measured by a sequential treatment by using the plurality of magnetic beads to which the plurality of substances to be measured can be bonded.

Second Embodiment

Next, a description will be given of Second Embodiment of the present invention. Note that a pretreatment method according to Second Embodiment is performed by the automatic analyzer illustrated in FIG. 1.

Figure 7:
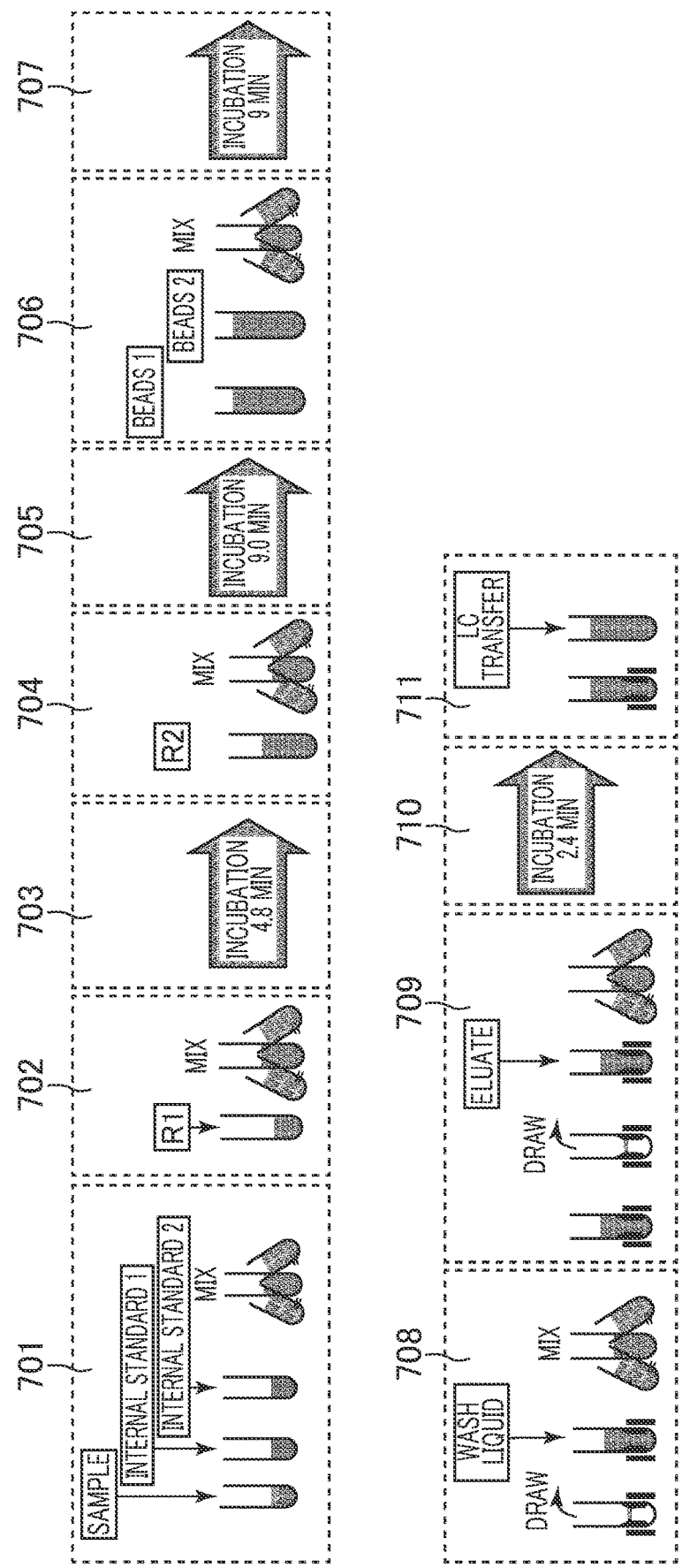
FIG. 7 is an explanatory view of an assay protocol of Second Embodiment, in which two types of magnetic beads are used.

FIG. 7 is an explanatory view of Second Embodiment, which is an explanatory view of an assay protocol when two types of magnetic beads (Functional Groups: Antibody Bead Types (each of the first magnetic beads and the second magnetic beads has a surface modified with an antibody as a functional group)) are used.

A description will be given below of a case where PTH as a type of parathyroid hormone and 25-OH vitamin D3 as a type of fat-soluble vitamin are used as substances to be measured.

The PTH is a factor that adjusts metabolism of calcium and a phosphoric acid in blood, which is a substance contributing to a thyroid disease or cancer. The vitamin D is a factor that adjusts metabolism of an amount of calcium in blood, which is a substance contributing not only to osteoporosis, but also to cancer, diabetes, and the like.

In Second Embodiment, antibody beads capable of selectively capturing the PTH and antibody beads capable of selectively capturing the vitamin D3 are used. The assay protocol requires a total of 53 cycles, and requires 31.8 minutes. A time period of each one of the cycles is set to 36 seconds. In Second Embodiment, each one of the cycles is set to 36 seconds, but each one of the cycles may also be longer or shorter than 36 seconds. The following will describe each of the cycles. Treatment steps 701-711 are pretreatment steps when the two types of magnetic beads are used in Second Embodiment. However, it is also possible to define the treatment steps 701-709 as pretreatment steps when the two types of magnetic beads are used in Second Embodiment.

In Cycles 1-2 (the treatment step 701), addition and stirring of the sample, the first internal standard substance, and the second internal substance is performed.

In Cycle 3 (the treatment step 702), addition and stirring of the first reagent is performed.

In Cycles 4-11 (the treatment step 703), incubation is performed (4.8 minutes).

In Cycle 12 (the treatment step 704), addition and stirring of the second reagent is performed.

In Cycles 13-27 (the treatment step 705), incubation is performed (9.0 minutes).

In Cycles 28-29 (the treatment step 706), addition and stirring of the first magnetic beads and the second magnetic beads is performed.

In Cycles 30-44 (the treatment step 707), incubation is performed (9.0 minutes).

In Cycles 45-47 (the treatment step 708), addition and stirring of the cleaning liquid is performed.

In Cycle 48 (the treatment step 709), addition and stirring of the first eluate is performed.

In Cycles 49-52 (the treatment step 710), incubation is performed (4.8 seconds).

In Cycle 53 (the treatment step 711), transfer of the eluate to the HPLC section 130 is performed.

The sample added in Cycles 1-2 (the treatment step 701) is blood serum, and 100 µL of the blood serum was added. As the internal standard substance for the PTH, 1 µg/mL 15N labeled PTH was used, and 100 µL of 1 µg/mL 15N labeled PTH was added while, as the internal standard substance for the 25-OH vitamin D3, 100 µg/mL 25-OH vitamin D3-d6 was used, and 100 µL of 100 µg/mL 25-OH vitamin D3-d6 was added.

As the first reagent added in Cycle 3 (the treatment step 702), 10 µL of the 0.1% aqueous formic acid solution as the pH adjustment reagent was added. The incubation in the steps 703, 705, 707, and 710 was performed at 37° C.

The second reagent added in Cycle 12 (the treatment step 704) is not used in Second Embodiment, but typically serves as the second pH adjustment reagent, a protein denaturation reagent, or the like.

The first magnetic beads added in Cycle 28 (the treatment step 706) are magnetic beads each having, in a functional group, an antibody that specifically binds to the PTH, and 50 µL of the magnetic beads were added.

The magnetic beads 2 added in Cycle 29 are magnetic beads each having, in a functional group, an antibody that specifically binds to the 25-OH vitamin D3, and 50 µL of the magnetic beads were added.

The cleaning liquid added in Cycles 45-47 (the treatment step 708) is pure water, and 100 µL of the pure water was added. The eluate 1 added in Cycle 48 (the treatment step 709) is a 0.1% glycine sodium solution (pH 10.0) as a high pH solution, and 50 µL of the 0.1% glycine sodium solution was added.

Since the substances to be measured in First Embodiment and the substances to be measured in Second Embodiment are different from each other, the two types of magnetic beads are used in each of First and Second Embodiments, but the types of the magnetic beads in Second Embodiment are different from the types of the magnetic beads in First Embodiment.

In First Embodiment, after the first magnetic beads are added in the step 606 and stirred, the incubation is performed in the treatment step 607. Subsequently, the second magnetic beads are added in the treatment step 608 and stirred, and then the incubation is performed in the treatment step 609.

By contrast, in Second Embodiment, the first magnetic beads and the second magnetic beads are added in the treatment step 706 and stirred, and then the incubation is performed in the treatment step 707.

In First Embodiment, since the two types of eluates are used, the addition and stirring of the first eluate is performed in the treatment step 611, the incubation is performed in the treatment step 612, and the transfer of the eluate to the HPLC section 130 is performed in the treatment step 613. Then, the addition and stirring of the second eluate is performed in the treatment step 614, the incubation is performed in the treatment step 615, and the transfer of the eluate to the HPLC section 130 is performed in the treatment step 616.

By contrast, in Second Embodiment, since the one type of eluate is used, the addition and stirring of the first eluate is performed in the treatment step 709, the incubation is performed in the treatment step 710, and the transfer of the eluate to the HPLC section 130 is performed in the treatment step 711.

Accordingly, in First Embodiment, the assay protocol requires a total of 74 cycles, and requires 44.4 minutes.

Meanwhile, in Second Embodiment, the assay protocol requires a total of 53 cycles, and requires 31.8 minutes. The treatment time period in Second Embodiment is shorter than the treatment time period in First Embodiment.

In other words, according to the present invention, when the substances to be measured differ, it is possible to further reduce the treatment time period.

Third Embodiment

Next, a description will be given of Third Embodiment of the present invention. Note that a pretreatment method according to Third Embodiment is also performed by the automatic analyzer illustrated in FIG. 1.

Third Embodiment relates to an assay protocol when one type of magnetic beads are used. The magnetic beads in Third Embodiment are of one type, and the magnetic beads each having a surface modified with a plurality of functional groups are used.

Figure 8B:
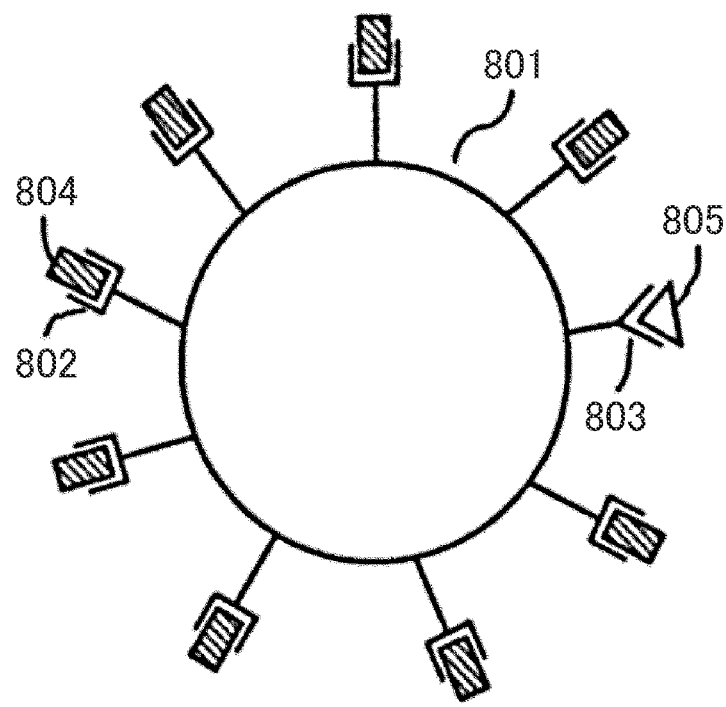
FIG. 8B is a view illustrating a concept of a magnetic bead having a plurality of functional groups in Third Embodiment.
Figure 8C:
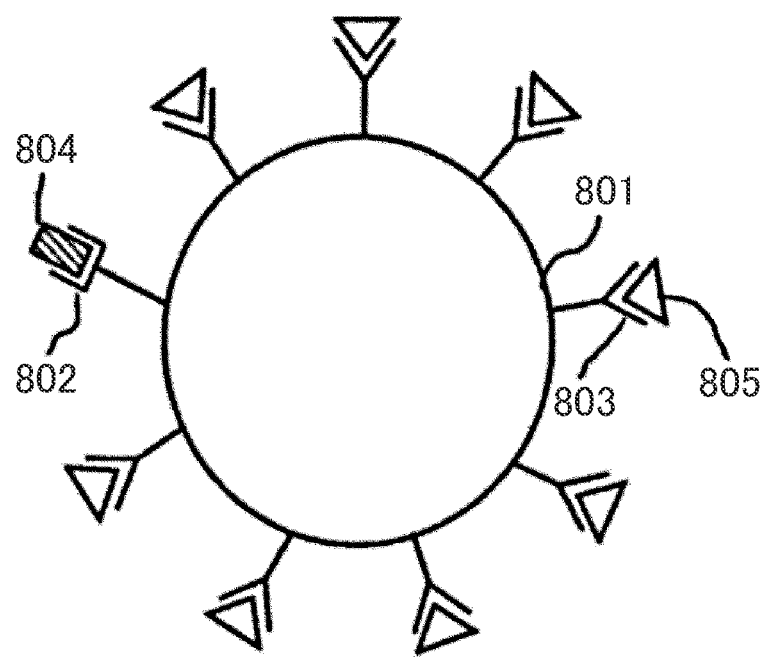
FIG. 8C is a view illustrating a concept of a magnetic bead having a plurality of functional groups in Third Embodiment.

FIGS. 8A, 8B, and 8C are diagrams each illustrating a concept of the magnetic beads having the plurality of functional groups in Third Embodiment.

As illustrated in FIG. 8A, as the magnetic beads used in Third Embodiment, magnetic beads 801 are modified with an antibody A 802 (first antibody) and an antibody B 803 (second antibody). To the antibody A 802, a substance to be measured A 804 (first-type substance to be measured) specifically binds while, to the antibody B 803, a substance to be measured B 805 (second-type substance to be measured) specifically binds.

In Third Embodiment, a description will be given of a case where, as the substance to be measured A 804, PTH as a type of thyroid hormone is used and, as the substance to be measured B 805, 25-OH vitamin D3 as a type of fat-soluble vitamin is used.

The surface of each of the magnetic beads 801 is modified with an antibody that specifically binds, as the antibody A 802, to the PTH and with an antibody that specifically binds, as the antibody B 803, to the 25-OH vitamin D3.

An able-bodied male has a blood concentration of the PTH which is 10-65 µg/mL and a blood concentration of the 25-OH which is 15-40 ng/ml, and there is an about 1000-fold concentration difference therebetween.

Accordingly, as illustrated in FIG. 8B, a quantity ratio of the antibody A 802 with which the surface of each of the magnetic beads 801 is modified to the antibody B 803 is increased to, e.g., about 1000.

Adjustment of the quantity ratio of the antibody A 802 to the antibody B 803 is not limited to that in the example illustrated in FIG. 8B. Depending on the blood concentration ratio between the substance to be measured A 804 and the substance to be measured B 805, it may also be possible to reduce the quantity ratio of the antibody A 802 with which the surface of each of the magnetic beads 801 is modified to the antibody B 803, as illustrated in FIG. 8C.

Alternatively, as illustrated in FIG. 8A, the quantity ratio of the antibody A 802 with which the surface of each of the magnetic beads 801 is modified to the antibody B 803 may also be adjusted to 1.

FIG. 9 is a conceptual view illustrating quantity ratios between substances to be measured before and after a pretreatment in which the magnetic bead 801 having the plurality of functional groups in Third Embodiment is used.

In FIG. 9, (A) illustrates a graph 901 representing a relationship between the substances to be measured and the concentrations thereof in blood (a sample), while (B) illustrates a graph 902 representing a relationship between the substances to be measured and concentrations thereof in an eluate after the pretreatment.

At the blood concentrations in blood (in the sample) before the pretreatment illustrated in (A) in FIG. 9, a concentration 903 of a substance to be measured A is lower than a concentration 904 of a substance to be measured B in blood (in the sample).

By pretreating the substances to be measured A and B by using the magnetic beads 801 in Third Embodiment, as illustrated in (B) in FIG. 9, it is possible equalize a concentration 905 of the substance to be measured A in the eluate and a concentration 906 of the substance to be measured B in the eluate.

In other words, by adjusting the quantity ratio between the antibody A and the antibody B of each of the magnetic beads 801, it is possible to equalize a concentration ratio between the plurality of substances to be measured that are contained in the eluate after the pretreatment and improve measurement accuracy.

As illustrated in FIG. 5, the assay protocol in Third Embodiment performs the treatment steps 501 to 511 when the one type of magnetic beads are used. However, in the case of Third Embodiment, the one type of magnetic beads 801 in use are each modified with the antibodies that bind to the plurality of types of substances to be measured. Therefore, it is possible to treat the plurality of types of substances to be measured, improve a throughput, and equalize the concentration ratio between the plurality of substances to be measured, which allows an improvement in measurement accuracy.

The assay protocol in Third Embodiment may also perform, depending on the types of the substances to be measured, the treatment steps 501 to 511 illustrated in FIG. 5, and perform treatment the steps 611 to 616 illustrated in FIG. 6.

According to Third Embodiment, it is possible to not only obtain the same effects as obtained from First and Second Embodiments, but also improve the measurement accuracy, as described above.

Note that, in Third Embodiment, the description has been given of the magnetic beads 801 of one type each having the surface modified with the two types of functional groups. However, the functional groups are preferably of at least two or more types, and may be of, e.g., three types or four types.

According to the present invention described heretofore, it is possible to perform a pretreatment method of an automatic analyzer that binds a substance to be measured to each of magnetic beads to perform treatment and full-automatically performs a batch step including pretreatment and a liquid chromatograph mass spectrometer, in which a plurality of magnetic beads to which a plurality of the substances to be measured can be bound are used to allow a plurality of substances to be measured to be pretreated by a sequential treatment.

The following is a detailed description further given of the effects of the present invention.

The first effect is improving a throughput. In the automatic analyzer capable of full-automatically performing the batch step including the pretreatment and the HPLC/MS, due to introduction into the detector after column separation using the HPLC and mass separation using the MS, even when the plurality of substances to be measured are present in a mixed state in the solution after the pretreatment, the plurality of substances measured can be detected.

Therefore, by using a plurality of types of magnetic beads and a plurality of eluates, the plurality of substances to be measured can be pretreated in a sequential pretreatment (assay protocol).

By using the plurality of types of magnetic beads, the number of cycles in one assay protocol is increased but, since the plurality of substances to be measured can be treated, by performing the pretreatment in parallel, the number of tests per time period increases to improve the throughput. Note that one assay protocol refers to a procedure from addition of a sample, followed by the end of the pretreatment, to introduction of a solution after the pretreatment into a separation/detection step.

One assay protocol includes a plurality of cycles. Each of the cycles takes the same time period and, by continuously performing respective operations in the individual cycles, one assay protocol is performed.

The second effect is allowing a reduction in the quantity of a sample for each of the testable substances to be measured. When a pretreatment is performed using a plurality of magnetic beads in one assay protocol, the quantity of the sample used in one assay protocol is the same, and accordingly a small quantity of the sample is sufficient to allow each of the testable substances to be measured to be inspected.

Finally, it is possible to adjust the concentrations of the substances to be measured in an eluate after the pretreatment and improve inspection accuracy. By using the contents of the plurality of substances to be measured in the sample to adjust the quantity of magnetic beads to be added to each of the substances to be measured, it is possible to adjust the contents of the substances to be measured which are contained in a solution after the pretreatment.

Specifically, the quantity ratio of the magnetic beads to be added to the lower-concentration substance to be measured is increased, while the quantity ratio of the magnetic beads to be added to the higher-concentration substance to be measured is reduced. Alternatively, the concentration of the magnetic beads to be stored in the measuring reagent container relative to the lower-concentration substance to be measured is increased, while the concentration of the magnetic beads to be stored in the measuring reagent container relative to the higher-concentration substance to be measured is reduced. Still alternatively, the concentrations of the individual magnetic beads and the quantities thereof to be added are adjusted.

Since the quantities of the substances to be measured which are contained after the pretreatment can be equalized, it is possible to reduce the influence of ionization efficiency in a MS ion source as a major cause of fluctuations, and consequently inspection accuracy is improved.

Note that, as the magnetic beads, two or more types can be used. Meanwhile, two or more types of substances to be measured may also be used.

In First and Second Embodiments, the first magnetic beads that bind to the first type substance to be measured and the second magnetic beads that bind to the second type substance to be measured can also be configured such that, depending on a blood concentration ratio between the plurality of types of substances to be measured which are contained in the sample described above, the respective concentrations of the first magnetic beads and the second magnetic beads, which are contained in each of the measuring reagent containers 118, or the respective quantities thereof to be added are adjusted.

LIST OF REFERENCE SIGNS

1 Automatic analyzer
101 Analysis section
102 Control section
103 Input section
104 Display section
110 Pretreatment section
111 Sample container
112 Sample container transport mechanism
113 Sample dispensing mechanism
114 Reaction container
115 Reaction container mounting rack
116 Reaction container transport mechanism
117 Reaction container disk
118 Measuring reagent container
119 Reagent disk
120 Reagent dispensing mechanism
121 Stirring mechanism
122 First magnetism collecting mechanism
123 First transport mechanism
124 Effluent dispensing mechanism
125 Second magnetism collecting mechanism
126 Second transport mechanism
127 Eluate dispensing mechanism
130 HPLC Section
140 Detector
201 Pump
202 Pressure sensor
203 Injection valve
204 Column
205 Column oven
206 Sample vial
207 Syringe
501 to 511, 601 to 616, 701 to 711 Treatment step
801 Magnetic bead
802 Antibody A
803 Antibody B
804 Substance A to be measured
804 Substance B to be measured
903 Concentration of substance A to be measured in blood (in sample)
904 Concentration of substance B to be measured in blood (in sample)
905 Concentration of substance A to be measured in eluate
906 Concentration of substance B to be measured in eluate

What is claimed is:

1. A method of pretreating a sample for an automatic analyzer comprising the steps of:
in one assay protocol, which includes a plurality of cycles in a predetermined time:
adding first magnetic beads to the sample, which contains a plurality of substances to be measured, the first magnetic beads each having surfaces modified with an antibody as a functional group that specifically binds to a structure of a first substance to be measured among the plurality of substances to be measured in the sample;
adding second magnetic beads to the sample, the second magnetic beads each having surfaces modified with an octadecylsilyl group that specifically binds to a second substance to be measured among the plurality of substances to be measured in the sample;
extracting the first magnetic beads and the second magnetic beads from the sample; and
separating, by a first eluate, the first substance to be measured from the first magnetic beads;
transferring the first eluate to a mass spectrometer; and
after transferring the first eluate to the mass spectrometer, separating, by a second eluate, the second substance to be measured from the second magnetic beads,
wherein each step is performed in one or more of the cycles of the one assay protocol.

2. The method of pretreating the sample for an automatic analyzer according to claim 1,
wherein the first eluate corresponds to the first magnetic beads and the second eluate, which is different than the first eluate, corresponds to the second magnetic beads.

3. The method of pretreating the sample for an automatic analyzer according to claim 1,
wherein the first magnetic beads and the second magnetic beads are housed in a measuring reagent container,
wherein concentrations of the first magnetic beads and the second magnetic beads are based on blood concentrations of the plurality of types of substances to be measured contained in the sample.

4. The method of pretreating the sample for an automatic analyzer according to 1,
wherein the first magnetic beads and the second magnetic beads are housed in a measuring reagent container,
wherein addition amounts of the first magnetic beads and the second magnetic beads are based on blood concentrations of the plurality of types of substances to be measured contained in the sample.

5. A method of pretreating a sample for an automatic analyzer comprising the steps of:
in one assay protocol, which includes a plurality of cycles in a predetermined time:
adding first magnetic beads to the sample, which contains a plurality of substances to be measured, the first magnetic beads each having surfaces modified with an antibody as a functional group that specifically binds to a structure of a first substance to be measured among the plurality of substances to be measured in the sample;
adding second magnetic beads to the sample, the second magnetic beads each having surfaces modified with a reverse phase mode functional group that specifically binds to a second substance to be measured among the plurality of substances to be measured in the sample;
extracting the first magnetic beads and the second magnetic beads from the sample; and
separating, by a first eluate, the first substance to be measured from the first magnetic beads;
transferring the first eluate to a mass spectrometer; and
after transferring the first eluate to the mass spectrometer, separating, by a second eluate, the second substance to be measured from the second magnetic beads, wherein each step is performed in one or more of the cycles of the one assay protocol.

* * * * *